United States Patent [19]

Wang et al.

[11] Patent Number: 5,091,206
[45] Date of Patent: Feb. 25, 1992

[54] PROCESS FOR PRODUCING MAGNETICALLY RESPONSIVE POLYMER PARTICLES AND APPLICATION THEREOF

[75] Inventors: Chao-Huei Wang, Gurnee; Dinesh O. Shah, Vernon Hills, both of Ill.

[73] Assignee: Baxter Diagnostics Inc., Deerfield, Ill.

[21] Appl. No.: 337,511

[22] Filed: May 30, 1989

Related U.S. Application Data

[62] Division of Ser. No. 113,294, Oct. 26, 1987, abandoned.

[51] Int. Cl.$^5$ .......................... A01N 1/02; B05D 5/12; B05D 7/00
[52] U.S. Cl. ......................................... 427/2; 427/128; 427/131; 427/214; 427/222
[58] Field of Search ................. 427/127–131, 427/212, 214, 216, 217, 221, 222, 338, 404, 405, 407.1, 409, 414, 419.2, 2; 252/62.51, 62.53–62.56

[56] References Cited

U.S. PATENT DOCUMENTS

| | | | |
|---|---|---|---|
| 4,177,253 | 12/1979 | Davies et al. | 436/527 |
| 4,490,436 | 12/1984 | Kawakami et al. | 428/403 |
| 4,628,037 | 12/1986 | Chagnon et al. | 436/526 |

FOREIGN PATENT DOCUMENTS

83/03920 11/1983 World Int. Prop. O.

Primary Examiner—Esther L. Kepplinger
Assistant Examiner—Joantha M. Stall
Attorney, Agent, or Firm—Kent Barta; Paul C. Flattery; Susan B. Fentress

[57] ABSTRACT

This invention provides a novel process of producing magnetically responsive polymer particles comprising polymeric core particles coated evenly with a layer of polymer containing magnetically responsive metal oxide. A wide variety of polymeric particles with sizes ranging from 1 to 100 microns can be used a core particles and transformed into magnetically responsive polymer particles. The surface of these magnetically responsive polymer particles can be coated further with another layer of functionalized polymer. These magnetically responsive polymer particles can be used for passive or covalent coupling of biological material such as antigens, antibodies, enzymes of DNA/RNA hybridization and used as solid phase for various types of immunoassays, DNA/RNA hybridization probes assays, affinity purification, cell separation and other medical, diagnostic, and industrial applications.

5 Claims, 2 Drawing Sheets

PROCESS FOR PRODUCING MAGNETICALLY RESPONSIVE POLYMER PARTICLES AND APPLICATION THEREOF

This is a divisional of U.S. patent application Ser. No. 113,294, filed Oct. 26, 1987, now abandoned.

FIELD OF THE INVENTION

This invention relates to a process to make magnetically responsive polymer particles and their use in immunoassays, biomedical and industrial applications.

BACKGROUND OF THE INVENTION

Many biological techniques, such as immunoassays, affinity purification etc., require the separation of bound from free fractions. Magnetic particles have been used to facilitate the desired separation.

Magnetic particles have been formed from a variety of particulate and magnetic matter, using a variety of processes, having different characteristics. For example, Ikeda et al. U.S. Pat. No. 4,582,622, discloses a magnetic particle comprised of gelatin, water-soluble polysaccharide, sodium phosphate and ferromagnetic substances; U.S. Pat. Nos. 4,628,037 and 4,554,088 disclose magnetic particles comprised of a magnetic metal oxide core surrounded by a coat of polymeric silane; U.S. Pat. No. 4,452,773 discloses discrete colloidal sized particles having a core of ferromagnetic iron oxide ($Fe_3O_4$) which is coated with a water-soluble polysaccharide or a derivative thereof having functional groups; and Mansfield U.S. Pat. No. 4,297,337 discloses magnetic glass- or crystal-containing material as a particulate carrier.

SUMMARY OF THE INVENTION

The present invention provides a novel process of producing magnetically responsive polymer particles, hereinafter referred to as magnetic particles, from polymeric particles with average size from about 1 to 100 microns in diameter regardless of shape and composition. The magnetic particles of this invention may be prepared by first producing magnetically responsive metal oxide, hereinafter referred to as metal oxide, with average size of about 1 micron or less and then coating a polymeric core particle with a layer of polymer containing metal oxide. The surface of these magnetic particles can be coated further with another layer of polymer or functionalized polymer to provide the desired surface characteristics.

The magnetic particles produced by the present invention are monodispersed in size with rough surface and have a magnetic metal oxide content of from about 5% to 50%, preferably from 10% to 25%. Particles with these characteristics have been found to be useful in immunoassays and a wide variety of biomedical applications. These magnetic particles can be used for passive or covalent coupling of biological material such as antigens, antibodies, enzymes or DNA/RNA and used as solid phase for various types of immunoassays, DNA/RNA hybridization assays, affinity purification, cell separation and other biomedical applications. The magnetic particles can also be used for industrial application such as the treatment of industrial waste.

OBJECTIVES AND ADVANTAGES

It is the objective of this invention to:

Develop a process of producing magnetically responsive polymer particles easily from readily available polymer particles.

Develop a process of producing magnetically responsive polymer particles with moderate sedimentation and fast magnetic separation.

Develop a process of producing magnetically responsive polymer particles with various surface charges, and functional groups for passive adsorption or covalent coupling of biological material.

Develop medical, biological, diagnostic and industrial applications using these magnetically responsive polymer particles.

The advantages of this invention include:

A wide variety of polymeric core particles with size from about 1 to 100 microns can easily be transformed to magnetically responsive particles.

The metal oxide content can be varied according to the applications.

The surface can be derivatized into a wide variety of functional groups for covalent coupling.

A wide variety of monomer can be used for the final coating to provide different surface characteristics of the resulting polymer.

Both crosslinked and noncrosslinked magnetically responsive polymer particles can be produced.

Monodispersed magnetically responsive polymer particles can be produced.

DETAILED DESCRIPTION OF THE INVENTION

The magnetic particles of this invention may be prepared by first producing metal oxide with average size of about 1 micron or less. The metal oxide is produced by heating and precipitating a mixture of divalent and trivalent metal salt, preferably a mixture of ferrous and ferric sulfate or chloride with sodium hydroxide solution. The molar ratio of divalent to trivalent metal salt can be varied from 0.5 to 2.0, preferably 0.5 to 1.0, to obtain the desirable size and magnetic characteristics of metal oxide. It is observed that the molar ratio of divalent to trivalent metal salt affects the size of the metal oxide: the smaller the molar ratio of divalent to trivalent metal salt, the smaller the size of metal oxide. The molar ratio of divalent to trivalent metal salt also affects the color of the resulting magnetic particles: the smaller the molar ratio, the lighter the brownish color of the resulting magnetic particles. Preferably, the metal oxide is either superparamagnetic or paramagnetic although ferromagnetic metal oxide can also be used, provided centrifugation instead of magnetic separation is used during the clean up. Other divalent transition metal salts such as manganese, magnesium, cobalt, nickel, zinc, and copper salts may be substituted for ferrous salt.

After the metal oxide has been precipitated, it is washed several times with centrifugation at $250 \times g$ until the supernatant is neutral in pH. The metal oxide is resuspended in deionized water and mechanically stirred at high speed to break down the aggregate of metal oxide crystals. Further centrifugation at $250 \times g$ will not pellet all of the metal oxide. The supernatant which contain smaller size metal oxide crystals is collected and the pellet is resuspended in deionized water. This process is repeated for at least three times or until most of metal oxide can no longer be pelleted at $250 \times g$. The metal oxide obtained this way usually has size less than 2.0 micron. Low speed centrifugation at $100 \times g$ to remove largers crystals will reduce the size to less than 0.8 micron.

The metal oxide with average size of 1.0 micron or less is mixed with monomer and coated onto the polymeric core particles, preferably polystyrene particles, with size of 1 to 100 microns in the presence of initiator. Addition of a small quantity of emulsifier will help prevent the particles from agglomerating. The magnetic particles are then coated with a protective layer of polymer, preferably polystyrene, to prevent the metal oxide from falling off. If functionalized magnetic particles are desired the magnetic particles can be coated further with another layer of functionalized polymer to provide functional groups such as carboxyl, amino or hydroxyl for covalent coupling of biological material.

Figures 1, 2:
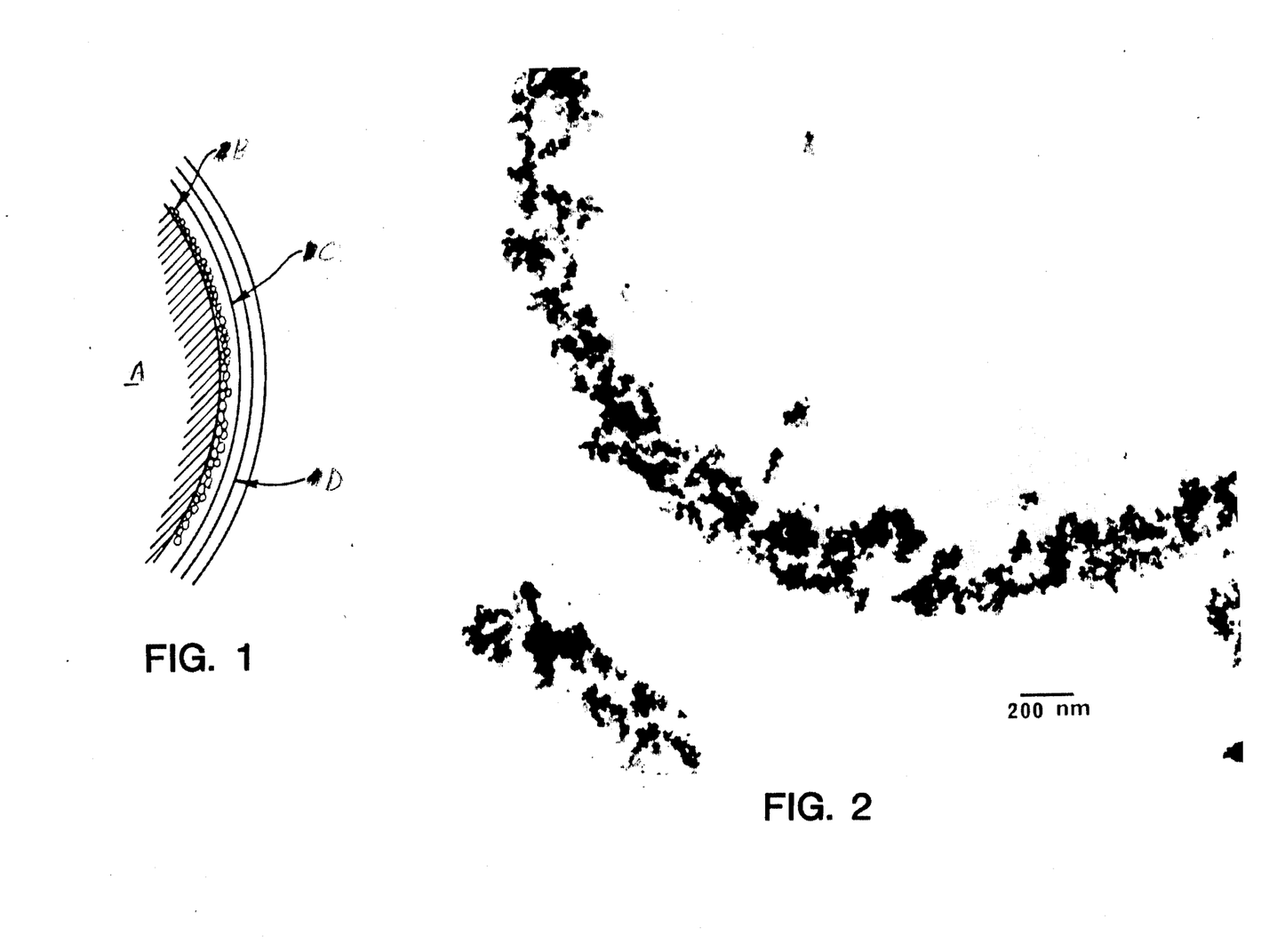
Figure 3A:
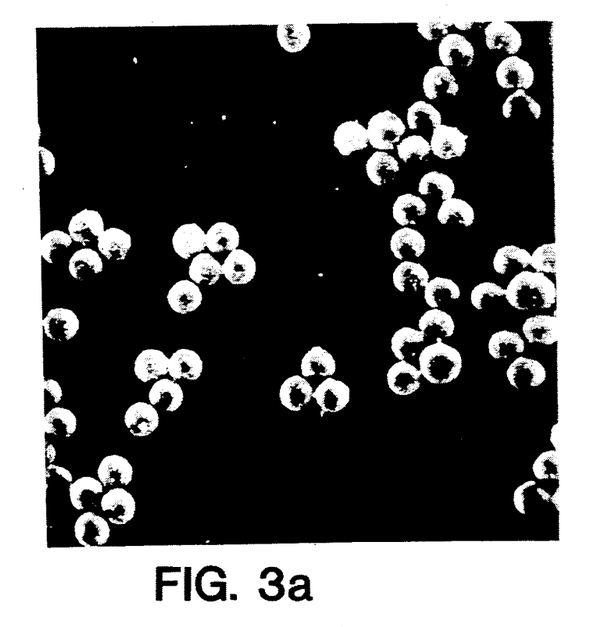
Figure 3B:
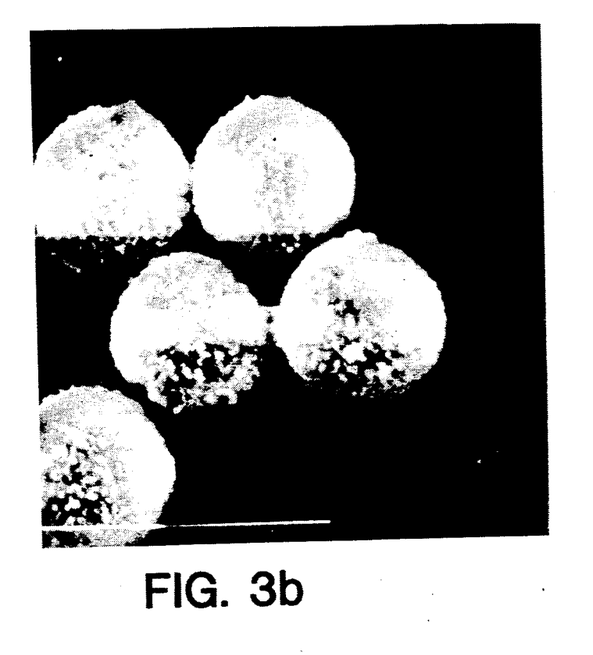

The magnetic particles prepared according to this invention can be illustrated in FIG. 1, where A represents the core particle, B represents the metal oxide/polymer coating, C represents the protective polymer coating and D represents the functionalized polymer coating. FIG. 2 shows the transmission electron micrograph of 0.08 to 0.1 micron slice of a magnetic particle prepared according to this invention. FIG. 3 shows a scanning electron micrograph of 6.8 micron magnetic particles, prepared according to this invention. FIG. 3$a$ is at 1000× and FIG. 3$b$ is at 5000× magnification.

The polymeric core particles useful in this invention may be of any polymer which can be obtained as a dispersion of small particles and which can absorb a monomer thereby causing the metal oxide and monomer mixture to coat onto the surface of the core particles. The core particles may be of any size and shape, preferably of 1 to 100 microns in size and spherical in shape. When monodispersed core particles are used the resulting magnetic particles will also be monodispersed in size. The core particles may be obtained by emulsion polymerization, suspension polymerization or other means of polymerization with or without a crosslinking agent such as divinyl benzene or the like. Among the monomers which can be used to prepare core particles are styrene, methyl methacrylate, vinyltoluene and the like. A mixture of the monomers can also be used. The monomer used for magnetic metal oxide coating or protective coating may or may not be the same type as the core particles. The weight ratio of monomer used for metal oxide coating to core particles may be from 0.1 to 12, preferably from 0.2 to 6, depending upon the thickness of metal oxide/polymer layer desired. When the metal oxide prepared from a mixture of ferrous and ferric salts is used for coating it is preferred to use a monomer to core particle weight ratio of about 0.1 to 0.5. However when the metal oxide prepared from a mixture of manganese (II) and ferric salts is used for coating the weight ratio of monomer to core particles may be from 0.1 to 12. As a result when crosslinked magnetic particles which are inert to common organic solvents are desired, it is prefered to use the metal oxide prepared from a mixture of manganese (II) and ferric salts with monomer containing 2% to 10%, preferably 8% to 10% by weight of crosslinking agent and a monomer to core particle weight ratio of 3 to 12, preferably 4 to 6. When lower monomer to core particle weight ratio (i.e. 0.1 to 0.5) is used during the metal oxide/polymer coating it is preferred to overcoat the resulting magnetic particles with a protective layer of polymer coating to further adhere the metal oxide to the surface of the magnetic particles. However, when higher monomer to core particle ratio (i.e. 3 to 12) is used no protective polymer coating is necessary. The polymerization temperature may be from 50° C. to 90° C., preferably 55° C. to 65° C. The polymerization initiator may either be water soluble such as potassium persulfate and the like or water insoluble such as benzoyl peroxide and the like. Other means of polymerization initiation such as radiation, ionization or the like may also be used. It is found unexpectly that magnetic particles can be produced without using any emulsifier when the metal oxide prepared from a mixture of manganese (11) and ferric salts is used for coating. However, a small amount of emulsifier such as sodium dodecylsulfate, Aerosol 22, Tween 20 or Nonidet P-40 (NP 40) is found to be useful in preventing the particles from extensive aggregation during the metal oxide/polymer coating when the metal oxide prepared from a mixture of ferrous and ferric salts is used for coating. Other emulsifiers with the same capability may also be used. The magnetic metal oxide content can be varied from 5% to 50%, preferably from 10% to 25% by using different amount of metal oxide during the metal oxide/polymer coating. Mutiple metal oxide/polymer coatings can also be employed to increase the metal oxide content. Other ingredients commonly used in polymerization may also be added as long as magnetic particles with desirable characteristics can be obtained. The ingredients for metal oxide/polymer coating may be added all at once at the beginning of metal oxide/polymer coating process or added stepwise. When the metal oxide prepared from a mixture of ferrous and ferric salt is used, it is preferred to add the ingredients stepwise. The ingredients may be mixed by mechanic stirring, tumbling or other means of agitation under vacuum or inert gas such as argon. The functional groups can be incorporated onto the surface of the magnetic particles by either using a mixture of monomer and functionalized monomer during the metal oxide/polymer coating or overcoating the magnetic particles with a thin layer of functionalized monomer at the end. The functionalized monomer used may be selected from one or a mixture of the following: 2-hyroxyethyl methacrylate, 2-aminoethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, glutaraldehyde and the like. The magnetic particles can also be overcoated with a layer of different polymer than the one used for metal oxide/polymer coating or protective coating to take up the surface characteristics of that polymer.

Applications of Magnetic Particles

The uses of a wide variety of magnetic particles as solid phase for various applications such as fluorescence immunoassays, radioimmunoassays, enzyme immunoassays, cell separations, enzyme immobilizations and affinity purifications have been reviewed in literature as examplified by the following articles: Hirschbein et al, Chemical Technology, March 1982, 172-179 (1982); Pourfarzaneh, The Ligand Quarterly, 5(1): 41-47 (1982); Halling and Dunnill, Enzyme Microbe Technology, 2: 2-10 (1980); Mosbach and Anderson, Nature, 270: 259-261 (1977); Guesdon et al, J. Allergy Clinical immunology, 61(1), 23-27 (1978). Some applications have also been disclosed in the U.S. Pat. Nos. 4,152,210 and 4,343,901 for enzyme immobilizations; U.S. Pat. Nos. 3,970,518, 4,230,685, and 4,267,2343 for cell separations; U.S. Pat. Nos. 4,554,088, 4,628,037, and 3,933,997 for immunoassays.

Some magnetic particles may be useful in one application, but not in another application. For example, the magnetic particles disclosed in U.S. Pat. No. 4,554,088 and 4,628,037, which comprise a superparamagnetic metal oxide core generally surrounded by a coat of polymeric silane, may be useful in immunoassay and affinity purification, due to the large surface area and slower settling rate, but are not suitable in cell separation application such as bone marrow purging. Due to the small size of the magnetic Particles, disclosed in these two patents, it is very difficult to remove all of the magnetic particles from the cell suspension effectively. Moreover, the nonspecific binding of smaller magnetic particles to normal cells would be much higher. In using magnetic particles for bone marrow purging, the magnetic particles are coated with antibody, such as sheep anti-mouse IgG, and the bone marrow is treated with a mixture of several monoclonal antibodies against the cancer cell surface antigens. The magnetic particles will bind only to the cancer cells and cause them to be separated from normal cells by passing them through a strong magnetic field. The cleansed cells are then put back into the patient.

By using the processes of this invention magnetic particles can be optimized in terms of size, surface area, metal oxide content and surface characteristics for a wide variety of biomedical applications. The magnetic particles produced by this invention can be used as solid phase for enzyme immunoassay, fluorescence immunoassay, radioimmunoassay, DNA/RNA hybridization assay, and other diagnostic applications. Immunoassays can be performed by using various configurations such as sandwich assays and competitive binding assays etc., which are obvious to those skilled in the art. The DNA/RNA hybridization can also be performed by using various configurations such as solid phase hybridization or liquid phase hybridization. In solid phase hybridization configuration a DNA or RNA probe (catcher probe) is immobilized on the magnetic particle first. The immobilized catcher probe is then used to hybridize with complimentary strand of DNA from the sample (sample DNA). Finally another probe (signal probe) which is labeled with fluorescent, radioactive or enzyme tracer and capable of hybridizing with another part of the sample DNA is used for signal generation. In liquid phase hybridization configuration the catcher probe and signal probe are allowed to hybridize with the sample DNA in the liquid phase first and then immobilized to the magnetic particles.

Alternatively, the signal probe can also be labelled with one or several biotin groups and the signal is detected by binding the biotin groups with avidin labelled fluorescent, radioactive or enzymatic tracer to enchance the sensitivity of the assay.

The immunoassays and DNA/RNA hybridization assays can be used to measure a wide variety of compounds such as drugs, hormones, antibodies, peptides, DNA, RNA, nucleotides, viral antigens, and carbohydrates in biological samples.

The magnetic particles produced by this invention can also be used for affinity purification, cell separation, enzyme immobilization and other biomedical applications. In cell separation the magnetic particles are used to either remove unwanted cells (negative selection) or enrich the wanted cells (positive selection) through immunological reactions or nonimmunological reactions. This principle can be used to remove cancer cells from bone marrow (bone marrow purging), purify cell populations through either positive or negative selection for tissue culture and perform various cellular immunoassays etc. In affinity purification the magnetic particles are used in place of conventional solid phase such as polyacrylamide gels, sepharose gels or other cellulose beads to purify a wide variety of biological materials such as antibodies, antigens, enzymes, inhibitors, cofactors, single stranded DNA, binding proteins, haptens and carbohydrates etc. In another application similar to the affinity purification, the magnetic particles can be used to cross adsorb and remove unwanted protein components from the antisera or clinical samples. In enzyme immobilization the enzyme is immobilize onto the magnetic particles through various means of coupling so as to preserve the enzyme activity and to permit the reuse of immobilized enzyme. The magnetic particles with immobilized enzyme can be used to replace other solid phases such as glass beads, controled pore glass, silica gels and cellulose beads etc., which are commonly used in immobilized enzyme systems to produce a wide variety of materials such as carbohydrates, amino acids, and proteins, etc.

The magnetic particles produced by this invention can be used for industrial applications like the treatment of industrial waste, to remove harmful chemicals, i.e. organic or inorganic solvents from industrial material.

These applications are all facilitated by the ease of separation, fast reaction rate and large surface area common to most of magnetic particles. The following examples are provided to further illustrate the versatility and advantages of this ivnention, the details thereof are not to be construed as limitations, for it will be apparent that various equivalents, changes and modifications may be resorted to without departing from the spirit and scope thereof and it is understood that such equivalent embodiments are intended to be included therein.

General Procedures for the Preparation of Metal Oxide

Example 1

In a three-necked round bottom flask equipped with mechanical stirrer, condenser, thermometer, dropping funnel and heating mantle was placed a mixture containing 0.361 mol of ferrous sulfate and 0.369 mol of ferric sulfate ($Fe^{++}/Fe^{+++}$ ratio=1) in 400 ml of deionized water. The mixture was heated to 85° to 90° C. with stirring and added dropwise 850 ml of 6 N sodium hydroxide over a period of 90 minutes. The mixture was stirred at 85° to 90° C. for one more hour and cooled to room temperature. The metal oxide precipitates were centrifuged at 250×g for 10 minutes. The clear supernatant was decanted and the pellet was resuspended in 900 ml of deionized water using mechanical stirrer. This cleaning process was repeated six times or until the supernatant was almost neutral in pH. The supernatant was decanted and resuspended in 200 ml of deionized water. Further centrifugation at 250×g will not pellet all of the metal oxide precipitates. The supernatant which contained smaller size metal oxide crystals was collected and the pellet was resuspended in 200 ml of deionized water. This process was repeated for at least three times or until most of metal oxide can no longer be pelleted at 250×g. The metal oxide obtained this way usually has size less than 2.0 micron. The combined metal oxide suspension was centrifuged at 100×g for 10 minutes. The supernatant was collected to give 800 ml of 8.6% w/v magnetic metal oxide suspension having the size less than 0.8 microns.

Example 2

Same procedures as described in Example 1 were followed except 0.235 mol of ferrous sulfate, 0.297 mol of ferric sulfate ($Fe^{++}/Fe^{+++}$ ratio=0.79) in 400 ml of deionized water and 480 ml of 6 N sodium hydroxide were used to give 2000 ml of 2.86% w/v suspension of magnetic metal oxide.

Example 3

Same procedures as described in Example 1 were followed except 0.178 mol of ferrous sulfate, 0.298 mol of ferric sulfate ($Fe^{++}/Fe^{+++}$ ratio=0.59) in 400 ml of deionized water and 520 ml of 6 N sodium hydroxide were used to give 1500 ml of 2.98% w/v suspension of magnetic metal oxide.

Example 4

Same procedures as described in Example 1 were followed except 0.15 mol of ferrous sulfate, 0.276 mol of ferric sulfate ($Fe^{++}/Fe^{+++}$ ratio=0.54) in 400 ml of deionized water and 520 ml of 6 N sodium hydroxide were used to give 700 ml of 6.88% w/v suspension of magnetic metal oxide.

Example 5

Same procedures as described in Example 1 were followed except 0.116 mol of manganese sulfate, 0.146 mol of ferric sulfate ($Mn^{++}/Fe^{+++}$ ratio=0.79) in 225 ml of deionized water and 240 ml of 6 N sodium hydroxide were used to give 1700 ml of 1.8% w/v suspension of magnetic metal oxide.

Preparation of Magnetic Particles

Example 6

A mixture containing 600 ml of deionized water, 6 ml of styrene and 80 ml of 8.6% w/v magnetic metal oxide prepared as described in Example 1, was placed in a sealed bottle. The bottle was evacuated and rotated at about 60 rpm in a 55° C. oven for one hour. To the mixture were added 12 g of potassium persulfate and 850 ml of 5% w/v, 4.0 micron polystrene particles. The bottle was resealed, evacuated and rotated for one hour and added 50 ml of 2% sodium dodecylsulfate. After five more hours 6 ml of styrene and 10 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 1.6 l with deionized water to give a 2.5% w/v suspension with about 11% magnetic metal oxide content and 4.3 micron average size.

Example 7

The magnetic particles, 1.6 l of 2.5% w/v, prepared as described in Example 6, were carboxylated by adding 1 g of sodium dodecylsulfate, 10 g of potassium persulfate and a solution containing 0.98 ml of undecylenic acid and 0.02 ml of divinyl banzene in 4 ml of methanol. The mixture was placed in a sealed bottle, evacuated and rotated at about 60 rpm in a 55° C. oven for 5 hours. The resulting carboxyl magnetic particles were separated magnetically and washed several times with deionized water until the supernatant was clear. The carboxyl magnetic particles were resuspended to 680 ml with deionized water to give a 5.8% w/v suspension with about 11% magnetic metal oxide content and 4.3 micron average size.

Example 8

A mixture containing 600 ml of deionized water, 6 ml of styrene and 80 ml of 8.6% w/v magnetic metal oxide prepared as described in Example 1, was placed in a sealed bottle. The bottle was evacuated and rotated at about 60 rpm in a 55° C. oven for one hour. To the mixture were added 12 g of potassium persulfate and 850 ml of 4.78% w/v, 6.1 micron polystrene particles. The bottle was resealed, evacuated, rotated for five hours and added 6 ml of styrene and 10 g of potassium persulfate. The mixture was rotated for another fifteen hours, filtered through two layers of cheese cloth, separated magnetically and washed several times with deionized water until the supernatant was clear. The resulting magnetic particles were resuspended to 1.5 l with deionized water and carboxylated by adding 1 g of sodium dodecylsulfate, 10 g of potassium persulfate and a solution containing 0.98 ml of undecylenic acid and 0.02 ml of divinyl benzene in 4 ml of methanol. The mixture was placed in a sealed bottle, evacuated and rotated at about 60 rpm in a 55° C. oven for 5 hours. The resulting carboxyl magnetic particles were separated magnetically and washed several times with deionized water until the supernatant was clear. The carboxyl magnetic particles were resuspended to 800 ml with deionized water to give a 4.3% suspension with about 11.6% magnetic metal oxide content and 6.8 micron average size.

Example 9

A mixture containing 600 ml of deionized water, 6 ml of styrene and 60 ml of 8.6% w/v magnetic metal oxide prepared as described in Example 1, was placed in a three-necked round bottom flask and stirred at 67° C. for one hour under argon. To the mixture were added 12 g of potassium persulfate and 470 ml of 5% w/v, 2.7 micron polystrene particles. The mixture was stirred at 67° C. for one hour and added 30 ml of 2% sodium dodecylsulfate. After stirring at 67° C. under argon for five more hours 6 ml of styrene and 6 g of potassium persulfate were added to the mixture. The mixture was stirred at 67° C. under argon for another fifteen hours, filtered through two layers of cheese cloth, separated magnetically and washed several times with deionized water until the supernatant was clear. The resulting magnetic particles were resuspended to 900 ml with deionized water and carboxylated by adding 0.6 g of sodium dodecylsulfate, 10 g of potassium persulfate and a solution containing 0.598 ml of undecylenic acid and 0.012 ml of divinyl benzene in 2.4 ml of methanol. The mixture was placed in a sealed bottle, evacuated and rotated at about 60 rpm in a 55° C. oven for 5 hours. The resulting carboxyl magnetic particles were separated magnetically and washed several times with deionized water until the supernatant was clear. The carboxyl magnetic particles were resuspended to 500 ml to give a 6.5% w/v suspension with about 14% magnetic metal oxide content and 4.0 micron average size.

Example 10

A mixture containing 600 ml of deionized water, 6 ml of styrene and 60 ml of 8.6% w/v magnetic metal oxide prepared as described in Example 1, was placed in a sealed bottle. The bottle was evacuated and rotated at about 60 rpm in a 55° C. oven for one hour. To the mixture were added 12 g of potassium persulfate and 470 ml of 5% w/v, 2.7 micron polystyrene particles. The bottle was resealed, evacuated and rotated for one hour and added 30 ml of 2% sodium dodecylsulfate. After five more hours 6 ml of styrene and 10 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 500 ml with deionized water to give a 6.8% w/v suspension with about 14% magnetic metal oxide content and 4.0 micron average size.

Example 11

A mixture containing 180 ml of deionized water, 2 ml of styrene and 20 ml of 8.6% w/v magnetic metal oxide, prepared as described in Example 1, was placed in a sealed bottle. The bottle was evacuated and rotated at about 60 rpm in a 55° C. oven for one hour. To the mixture were added 4 g of potassium persulfate and 160 ml of 6.8% w/v magnetic particles (3.0 micron, 14% metal oxide content), prepared as described in Example 10. The bottle was resealed, evacuated and rotated for one hour and added 10 ml of 2% sodium dodecylsulfate. After 5 more hours 2 ml of styrene and 2 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 160 ml with deionized water to give a 7.78% w/v suspension with about 19% metal oxide content and 4.2 micron average size.

Example 12

A mixture containing 90 ml of deionized water, 1 ml of styrene and 10 ml of 8.6% w/v magnetic metal oxide, prepared as described in Example 1, was placed in a sealed bottle. The bottle was evacuated and rotated at about 60 rpm in a 55° C. oven for one hour. To the mixture were added 1 g of potassium persulfate and 80 ml of 7.78% w/v magnetic particles (3.2 micron, 19% metal oxide content), prepared as described in Example 11. The bottle was resealed, evacuated and rotated for four hour and added 5 ml of 2% sodium dodecylsulfate. After 5 more hours 1 ml of styrene and 1 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 160 ml with deionized water to give a 4.5% w/v suspension with about 23% metal oxide content and 4.5 micron average size.

Example 13

A mixture containing 400 ml of deionized water, 1.92 ml of styrene, 0.08 ml of divinyl benzene, 4 g of potassium persulfate, 20 g of 200–400 mesh 4% divinyl benzene cross linked polystyrene beads and 10 ml of 8.6% w/v magnetic metal oxide, prepared as described in Example 1, was placed in a sealed bottle. The bottle was evacuated and rotated at about 60 rpm in a 55° C. oven for 15 hours. The mixture was allowed to settle and the supernatant was decanted. The resulting magnetic beads were resuspended in 200 ml of deionized water and allowed to settle again. This process was repeated several times until the supernatant was clear. The resulting magnetic beads were resuspended in 200 ml of deionized water and added 0.1 g of sodium dodecyl sulfate, 2.0 g of potassium persulfate, 0.48 ml of styrene, and 0.02 ml of divinyl benzene. The bottle was resealed, evacuated and rotated at about 60 rpm in a 55° C. over for one hour and added a solution containing 0.098 ml of undecylenic acid and 0.002 ml of divinyl benzene in 0.4 ml of methanol. The mixture was rotated for four more hours and cleaned up by gravitational sedimentation as described previously. The water was removed by filtration and the carboxyl magnetic beads were dried to give 20 g of 200–400 mesh carboxyl magnetic beads.

Example 14

A mixture containing 100 ml of deionized water, 0.5 ml of styrene, 2 g of potassium persulfate, 75 ml of 5% w/v 4.0 micron polystrene particles and 10 ml of 6.88% w/v magnetic metal oxide, prepared as descrived in Example 4, was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting magnetic particles were resuspended to 150 ml with deionized to give a 2.5% w/v suspension with about 14% metal oxide content and 4.3 micron average size.

Example 15

Same procedures as described in Example 14 were followed except 20 ml of 6.88% w/v magnetic metal oxide, prepared as described in Example 4, was used to give 160 ml of 2.5% w/v suspension with about 18% metal oxide content and 4.3 micron average size.

Example 16

A mixture containing 2000 ml of deionized water, 13 ml of styrene and 550 ml of 2.98% w/v magnetic metal oxide prepared as described in Example 3, was placed in a sealed bottle. The bottle was evacuated and rotated at about 60 rpm in a 55° C. oven for one hour. To the mixture were added 20 g of potassium persulfate and 950 ml of 10% w/v, 3.0 micron polystyrene particles. The bottle was resealed, evacuated and rotated for one hour and added 60 ml of 2% sodium dodecylsulfate. After five more hours 8 ml of styrene and 10 g of potassium persulfate were added to the mixture. The mixture was rotated for another fifteen hours, filtered through two layers of cheese cloth, separated magnetically and washed several times with deionized water until the supernatant was clear. The resulting magnetic particles were resuspended to 3000 ml with deionized water to give a 3.38% w/v suspension with about 12% magnetic metal oxide content and 3.2 micron average size.

Example 17

A mixture containing 150 ml of magnetic particles (3.2 micron, 3.38% w/v with 12% metal oxide content) prepared as described in Example 16, 2 ml of 1% NP 40, 0.5 ml of methyl methacrylate or styrene, 1 g of potassium persulfate and 2 ml of functionalized monomer, trimethylammoniumethyl methacrylate methosulfate (40% aqueous solution), was placed in a sealed bottle.

The bottle was rotated at about 60 rpm in a 55° C. oven for four hours. The mixture was filtered through two layers of cheese cloth, separated magnetically and washed several times with deionized water until the supernatant was clear. The resulting magnetic particles were resuspended to 200 ml with deionized water to give a 2.5% w/v suspension of magnetic particles with trimethylammonium functional groups on the surface.

Example 18

Same procedures as described in Example 17 were followed except 1 ml of functionalized monomer, 2-aminoethyl methacrylate, was used to give 200 ml of 2.5% w/v suspension of magnetic particles with amino groups on the surface.

Example 19

Same procedures as described in Example 17 were followed except 1 ml of functionalized monomer, 2-hydroxyethyl methacrylate, was used to give 200 ml of 2.5% w/v suspension of magnetic particles with hydroxyl groups on the surface.

Example 20

Same procedures as described in Example 17 were followed except 1 ml of monomer, 1-vinyl-2-pyrrolidinone, was used to give 200 ml of 2.5% w/v suspension of magnetic particles with polyvinylpyrrolidinone on the surface.

Example 21

Same procedures as described in Example 17 were followed except 1 g of functionalized monomer, methyl propene sulfonic acid, was used to give 200 ml of 2.5% w/v suspension of magnetic particles with sulfonic acids groups on the surface.

Example 22

Same procedures as described in Example 17 were followed except 1 ml of functionalized monomer, dimethylaminoethyl methacrylate, was used to give 200 ml of 2.5% w/v suspension of magnetic particles with dimethylamino groups on the surface.

Example 23

A mixture containing 20 ml of 7.0% w/v, 2.11 micron polystyrene particles, 100 ml of 1.8% w/v metal oxide prepared as described in Example 5, 50 ml of deionized water and a solution containg 0.15 g of benzoyl peroxide in 7.5 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting magnetic particles were resuspended to 200 ml with deionized water to give 5.0% w/v suspension with about 16.8% metal oxide content and 3.6 micron average size.

Example 24

A mixture containing 20 ml of 7.0% w/v, 2.11 micron polystyrene particles, 100 ml of 1.8% w/v metal oxide prepared as described in Example 5, 50 ml of deionized water and a solution containing 0.15 g of benzoyl peroxide and 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 5.0% w/v suspension with about 16.8% metal oxide content and 3.6 micron average size. The crosslinked magnetic particles prepared this way were found to be uniform in size and inert to common organic solvents such as acetone, acetonitrile and dimethyl formamide.

Example 25

A mixture containing 20 ml of 7.0% w/v, 2.11 micron polystyrene particles, 150 ml of 1.8% w/v metal oxide prepared as described in Example 5 and a solution containing 0.15 g of benzoyl peroxide, 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 5.4% w/v suspension with about 23% metal oxide content and 4.0 micron average size. The crosslinked magnetic particles prepared this way were found to be uniform in size and inert to common organic solvents such as acetone, actonitrile and dimethyl formamide.

Example 26

A mixture containing 15 ml of 9.16% w/v, 3.2 micron polystyrene particles, 100 ml of 1.8% w/v metal oxide prepared as described in Example 5, 55 ml of deionized water and a solution containing 0.15 g of benzoyl peroxide and 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 4.7% w/v suspension with about 16.8% metal oxide content and 5.5 micron average size., The crosslinked magnetic particles prepared this way were found to be uniform in size and inert to common organic solvents such as acetone, actonitrile and dimethyl formamide.

Example 27

A mixture containg 30 ml of 4.5% w/v, 4.1 micron polystyrene particles, 100 ml of 1.8% w/v metal oxide prepared as described in Example 5, 40 ml of deionized water and a solution containing 0.15 g of benzoyl peroxide and 0.75 ml of divinyl benzene in 6.75 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked magnetic particles were resuspended to 200 ml with deionized water to give 4.5% w/v suspension with about 16.9% metal oxide content and 6.7 micron average size. The crosslinked magnetic particles prepared this way were found to be unform in size and inert to common organic solvents such as acetone, acetonitrile and dimethyl formamide.

Example 28

A mixture containing 20 ml of 7.0% w/v, 2.11 micron polystyrene particles, 100 ml of 1.8% w/v metal oxide prepared as described in Example 5, 50 ml of deionized water and a solution containing 0.15 g of benzoyl peroxide, 0.75 ml of undecylenyl alcohol and 0.75 ml of divinyl benzene in 6 ml of styrene was placed in a sealed bottle. The bottle was evacuated and rotated at about 60 rpm in a 55° C. oven for fifteen hours. The mixture was filtered through two layers of cheese cloth, separated magnetically and washed several times with deionized water until the supernatant was clear. The resulting crosslinked hydroxyl magnetic particles were filtered and dried to give 9 g of powder with about 16.8% metal oxide content and 3.9 micron average size. The crosslinked hydroxyl magnetic particles prepared this way were found to be uniform in size and inert to common organic solvents such as acetone, acetonitrile and dimethyl formamide.

Coupling Biological Materials to Magnetic Particle

Example 29

In a 80 ml bottle was place 30 ml of 4.3 micron, 5.0% w/v carboxyl magnetic particles prepared as described in Example 7. The particles were separated magnetically and resuspended in 50 ml of phosphate buffer (0.1 M. pH 5.5). To the particle suspension were added 20 mg of bovine serum albumin and 100 mg of 1-ethyl-3-(3-dimethylaminopropyl)-carbodiimide (EDC). The mixture was rotated end to end at room temperature for two hours and separated magnetically. The particles were washed once with 80 ml of phosphate buffer and resuspended to 75 ml with phosphate buffered saline (0.1 M, pH.7.0) to give a 2.0% w/v suspension.

To couple bovine serum albumin to magnetic particles by passive adsorption the same procedures were followed except no EDC was used.

Example 30

In a 4 ml vial was placed 1 ml of 4.3 micron, 5.0% w/v carboxyl magnetic particles prepared as described in Example 7. The particles were separated magnetically and washed once with 2 ml of phosphate buffer (0.1 M, pH 5.5) and resuspended to 2 ml with the same buffer. To the particles suspension were added 140 ml of 1.4 mg/ml Goat (Gt) anti Mouse (Ms) IgG and 10 mg of 1-ethyl-3-(3-dimenthylaminopropyl) carbodiimide. The vial was rotated end to end at room temperature for two hours. The particles were separated magnetically, washed once with 2 ml of phosphate buffer and resuspended to 2 ml with phosphate buffered saline (0.1 M, pH 7.0) to give a 2.5% w/v Gt anti Ms IgG coated magnetic particles. Other kind of antibody either monoclonal or polyclonal could also be coupled to carboxyl magnetic particles by using the same procedures.

To couple Gt anti Ms IgG or other kind of antibody to the magnetic particles by passive adsorption the same procedures were followed except no EDC was used.

Example 31

In a 4 ml vial was placed a 2.5 ml of bovine serum albumin coated magnetic particles (4.3 micron, 2% w/v) prepared as described in Example 29. The particles were separated magnetically and resuspended to 2 ml with phosphate buffer (0.1 M, pH 5.5). To the mixture were added 10 ul of Ms anti B red cells surface antigen (20 mg/ml) and 1 mg of 1-ethyl-3-(3-dimethylaminopropyl)-carbodiimide. The mixture was rotated end to end at room temperature for two hours. The particles were separated magnetically, washed once with phosphate buffer and resuspended in 2 ml of phosphate buffered saline (0.1 M, pH 7.0) to give a 2.5% w/v suspension.

Example 32

Same procedures as described in Example 31 were followed except using 40 ul of Ms anti A red cells surface antigen (5 mg/ml) to give 2 ml of 2.5% w/v suspension.

Blood Typing Using Magnetic Particles

Example 33

In a 5 mm×65 mm test tube labeled A was placed 25 ul of 2.5% w/v Ms anti A coated magnetic particles prepared as described in Example 32. To the other test tube labeled B was placed 25 ul of 2.5% w/v Ms anti B coated magnetic particles prepared as described in Example 31. To both test tubes was added 50 ul of 1% packed red blood cells prepared by 1 to 100 dilution of packed red blood cells in isotonic buffered saline. The test tubes were shaked by finger tapping for several times and placed on the top of a magnet. The results were summarized as follows:

|  | BLOOD TYPE | | | |
| --- | --- | --- | --- | --- |
|  | A | B | O | AB |
| TUBE A | + | − | − | + |
| TUBE B | − | + | − | + |

Where + represent a positive reaction, meaning the red cells were agglutinated by the corresponding antibody coated magnetic particles as a result the supernatant in the test tube was clear after magnetic separation. On the other hand the supernatant of a negative reaction would remain cloudy after magnetic separation due to the absence of agglutination between the red cells and the antibody coated magnetic particles.

Immunoassays Using Magnetic Particles

Example 34

In a 2 ml microcentrifuge tube was placed 1 ml of 6% w/v, 3 micron carboxyl magnetic particles. The particles were centrifuged for 3 minutes at 10,000 rpm. The supernatant was aspirated and the particles were resuspended by vortexing with 1 ml of 5 to 100 ug/ml recombinant HBcAg in acetate buffer. The tube was rotated at toom temperature for two hours and centrifuged as described before. The supernatant was aspirated and the particles were resuspended in 1 ml of overcoat solution containing acetate buffer and 2 to 10% of normal animal serum. The tube was rotated at room temperature for 2 to 16 hours and centrifuged as described before. The supernatant was aspirated and the particles were washed three times with 1 ml of isotonic buffered slaine (IBS) by centrifugation and resuspension. Finally, the particles were resuspended with 1 ml of IBS and stored at 2° to 8° C.

Example 35

To the first two columns of a 96-well microtiter plate was placed 20 ul of 0.25% w/v heptitis B core antigen (HBcAg) coated magnetic particles prepared as described in Example 34. Sample preparation consisted of various dilutions of a HBcAb positive serum into a negative plasma, followed by a 1:100 dilution of each sample into specimen dilution buffer (SDB). The SDB contained phosphate buffer, protein stabilizers, detergent and antimicrobial agents. To the wells containing the particles were added 50 ul of each final sample dilution. After 30 minutes incubation at 37° C., the particles were separated for two minutes on a magnetic separator and washed three times with 200 ul wash buffer containing salts and detergent. To each well containing the particles was added 50 ul of goat antihuman IgG-B-D-galactosidase conjugate (0.5 ug/ml) in diluent containing salts, protein stabilizers, glycerol, detergent and antimicrobial agents. After 15 minutes incubation at 37° C. the particles were separated and washed three times as described above and resuspended in 30 ul of IBS. The particles were transferred to the first two columns of a black microtiter plate (Dynatech). To each well containing the particles was added 100 ul of a solution containing 4-methylumbelliferyl-B-galactopyranoside (MUG, Sigma). The plate was incubated at 37° C. and the fluorescence intensity was measured by using a Fluorescence Concentration Analyzer (FCA, Pandex) equipped with 365 nm excitation and 450 nm emmision filters at five minutes interval and 10 × gain setting. The increase in fluorescence intentsity in a five minutes interval was recorded in arbitrary fluorescence unit (AFU) and presented in Table I.

TABLE I

| Dilution of Positive Specimen | AFU (5 Minutes) Average of Two Wells |
|---|---|
| 1:100 | 22687 |
| 1:1000 | 5933 |
| 1:5000 | 1516 |
| 1:8000 | 835 |
| 1:10000 | 639 |
| 1:15000 | 495 |
| 1:20000 | 427 |
| 1:25000 | 307 |

Example 36

The coupling of mouse antiHBsAg to carboxyl magnetic particles was similar to Example 30.

To the wells of a black 96-well microtiter plate (Dynatech) were added 20 ul of 0.25% w/v, 3.2 micron, mouse antiHBsAg coated carboxyl magnetic particles in duplicate. To the wells containing the magnetic particles was added 100 ul of neat plasma containing various amounts of HBsAg or a HBsAg-negative plasma. After 30 minutes incubation at 37° C., the particles were separated for two minutes on a magnetic separator and washed once with 100 ul of wash buffer containing salts and detergent. To each will containing the particles was added 20 ul of mouse antiHBsAg--B-galactosidase conjugate in diluent containing salts, protein stabilizers, glycerol, detergent and antimicrobial agents. After 15 minutes incubation at 37° C., the particles were separated and washed five times as described above. To each will containing the particles was added 50 ul of a solution containing 4-methylumbelliferyl-B-D-galactopyranoside (MUG, Sigma). The plate was incubated at 37° C. and the fluorescence was measured by using a Fluorescence Concentration Analyzer (FCA, Pandex) equipped with 365 nm excitation and 450 nm emission filters ar five minutes interval and 10 × gain setting. The increase in fluorescence intentsity in a five minutes interval was recorded in arbitrary fluorescence unit (AFU) and Presented in Table II.

TABLE II

| HBsAg Conc. (nano gm) | AFU (5 Minutes) Average of Two Wells |
|---|---|
| 1.0 | 1149 |
| 0.5 | 455 |
| 0.25 | 218 |
| 0.125 | 118 |
| neg. | 14 |

Example 37

The HIV-1 antigens from HTLV-IIIB/H-9 cells (Gallo Strain) were coupled to 3.6 micron carboxyl magnetic particles by using similar procedures as described in Example 34.

To the wells of a 96-well microtiter plate were added 20 ul of 0.25% w/v of HIV coated magnetic particles in duplicate. To the wells containing the particles were added 50 ul of positive, borderline and negative specimens diluted 1:100 in specimen dilution buffer (SDB) containing phosphate buffer, protein stabilizers, detergent and antimicrobial agents. After 30 minutes incubation at 37° C., the particles were separated for two minutes on a magnetic separator and washed three times with 100 ul of washed buffer containing salts and detergent. To each well containing particles was added 50 ul of goat antihuman-B-galactosidase (approximately 0.5 ug/ml) conjugate in diluent containing salts, protein stabilizers, glycerol, detergent and antimicrobial agents. After 15 minutes incubation at 37° C., the particles were washed four times as described above. The particles were transferred to the black microtiter plate (Dynatech). To each well containing particles was added 100 ul of a solution containing 4-methylumbelliferyl-B-D-galactopyranoside (MUG, Sigma). The plate was incubated at 37° C. and the fluorescence intensity was measured by using a Fluorescence Concentration Analyzer (FCA, Pandex) equipped with 365 nm excitation and 450 nm emission filters at five minutes intervals and 25 × gain setting. The increase in fluorescence intensity in a five minutes interval was recorded in arbitrary fluorescence unit (AFU) and presented in Table III.

TABLE III

| Anti-HIV Specimens | AFU (5 minutes) Average of Two Wells |
|---|---|
| Positive Control | 9462 |
| Borderline Specimen | 527 |
| Negative Control | 86 |

Cell Separation Using Magnetic Particles

Example 38

The 4.3 micron carboxyl magnetic particles prepared as described in Example 7 were washed and sonicated in phosphate buffered saline (PBS, pH 7.7), sterilized in 70% ethanol for 10 minutes, washed three times in PBS and incubated for 48 hours at 4° C. with affinity-purified sheep anti-mouse immunoglobulin antibody (SAM) at 0.5 mg/ml and a ratio of 3.3 mg antibody/100 mg particles. Before use, the antibody coated magnetic particles were washed in PBS and resuspend at the desired concentration in PBS.

Human tissue culture cALLa-positive NALM-16 leukemia cells were washed and suspended in PBS. One fraction was not treated with antibody (−MoAb). The other fraction was treated with two anti-CD10 and one anti-CD9 monoclonal antibodies (+MoAb) for 30 minutes at 4° C., washed in PBS and adjusted to $3.5 \times 10^6$ cells/ml on PBS. To two tubes, one containing the antibody treated cells (+MoAb), the other containing untreated cells (−MoAb) were added SAM coated magnetic particles at a particle to starting cell ratio of 45. The tubes were rotated at 4° C. for 30 minutes. The particles were separated with a magnetic separator. The supernatant was collected and centrifuged to collect the remaining cells. The pellet was resuspended in 100 ul of trypan blue and total cell count was made. The results were present in Table IV.

TABLE IV

| Particle/cell Ratio | Cells +/− MoAb | Cells Received | % Depletion |
|---|---|---|---|
| 0 | + | $7.62 \times 10^5$ | 0 (Control) |
| 45 | + | $2.89 \times 10^4$ | 96.2 |
| 45 | − | $7.33 \times 10^5$ | 4.6 |

What is claimed is:

1. The process to make a magnetically responsive polymer particle having a polymeric core particle evenly covered by a metal oxide/polymer coating comprising
    producing a magnetic oxide particle with an average size of about 1 micron or less by heating an aqueous solution containing a mixture of divalent and trivalent transition metal salts in a molar ratio of divalent to trivalent metal salt of 0.5 to 2.0 under alkaline conditions to precipitate a metal oxide, washing said precipitate, breaking down the aggregate of said metal oxide crystals contained in said precipitate, and collecting the smaller sized metal oxide crystals of average size less than 1.0 micron,
    mixing said magnetic metal oxide particles with a monomer in a weight ratio of 0.1 to 12 to produce an admixture
    coating a polymeric core with said admixture in the presence of a polymerization initiator capable of initiating polymerization of said monomer.

2. The process of claim 1 together with the further step of coating further with a functionalized monomer to provide functional groups for covalent binding of biological materials.

3. The process to make a magnetically responsive polymer particle covered by a metal oxide/crosslinked polymer coating inert to common solvents comprising
    producing a magnetic oxide particle with an average size of about 1 micron or less by heating an aqueous solution containing admixture of divalent and trivalent transition metal salts in a molar ratio of divalent to trivalent metal salt of 0.5 to 2.0 under alkaline conditions to precipitate a metal oxide, washing said precipitate, breaking down the aggregate of said metal oxide crystals contained in said precipitate, and collecting the smaller sized metal oxide crystals of average size less than 1.0 micron,
    mixing said suspended metal oxide particle with a monomer in a weight ratio of 0.1 to 12, said monomer containing 8 to 10 percent of a cross-linking agent, to produce an admixture, and
    coating a polymeric core particle with said admixture in the presence of a polymerization initiator capable of initiating polymerization of said monomer.

4. The process of claims 1, 2 or 3 wherein said monomer is selected from the group consisting of styrene, methyl methacrylate, vinyltoluene, divinylbenzene, and glycidyl methacrylate.

5. The process of claim 2 wherein said function group is selected from the group consisting of carboxyl, amino, and hydroxyl.

* * * * *